United States Patent [19]

Kees, Jr.

[11] Patent Number: 4,827,930
[45] Date of Patent: May 9, 1989

[54] REINFORCING CLOSER FOR ANEURYSM CLIP

[75] Inventor: George Kees, Jr., Alexandria, Ky.

[73] Assignee: Codman & shurtleff, Inc., Randolph, Mass.

[21] Appl. No.: 392,743

[22] Filed: Jun. 28, 1982

[51] Int. Cl.$^4$ ............................................. A61B 17/12
[52] U.S. Cl. ................................. 128/325; 128/346
[58] Field of Search ............... 128/325, 326, 346, 354, 128/321, 20, 321; 294/995, 1 CA; 81/43, 424, 425 A; 267/164, 158; 269/164, 258; 24/253; 29/268; 433/3-5, 159

[56] References Cited

U.S. PATENT DOCUMENTS

| | | | |
|---|---|---|---|
| 1,142,817 | 6/1915 | Kirk, Jr. | 267/16 X |
| 2,079,711 | 5/1937 | Johnson et al. | 24/253 |
| 2,285,683 | 6/1942 | Seashore | 81/424 |
| 2,631,585 | 3/1953 | Siebrandt | 128/321 |
| 3,263,535 | 8/1966 | Zürcher | 81/424 |
| 3,293,958 | 12/1966 | Smith | 81/43 |
| 3,802,437 | 4/1974 | Kees, Jr. | 24/253 |
| 3,805,792 | 4/1974 | Cogley | 128/346 |
| 4,360,023 | 11/1982 | Sugita et al. | 128/325 |

FOREIGN PATENT DOCUMENTS

| | | | |
|---|---|---|---|
| 722712 | 3/1932 | France | 433/159 |
| 483977 | 12/1975 | U.S.S.R. | 128/346 |

OTHER PUBLICATIONS

"A New Clamp for Rapid Vascular Anastomis", Padila, M. D. et al., Surgery, vol. 57, No. 6, 6/1965, pp. 819–822.

Primary Examiner—C. Fred Rosenbaum
Assistant Examiner—J. L. Kruter
Attorney, Agent, or Firm—Roy F. Schaeperklaus; Paul A. Coletti

[57] ABSTRACT

A device for closing jaws of an aneurysm clip. The device includes a central spring portion. Body members are mounted on the central spring portion to be urged toward a closed position by the central spring portion. Heads carried by the body members are pivotally mounted on jaw members which engage the jaws of the aneurysm clip to urge the jaws to closed position. The body members are spaced to receive the aneurysm therebetween. The jaw members can move along the jaws to selected position, and a main portion of the device can be swung about pivots on the jaw members to selected angular position.

3 Claims, 1 Drawing Sheet

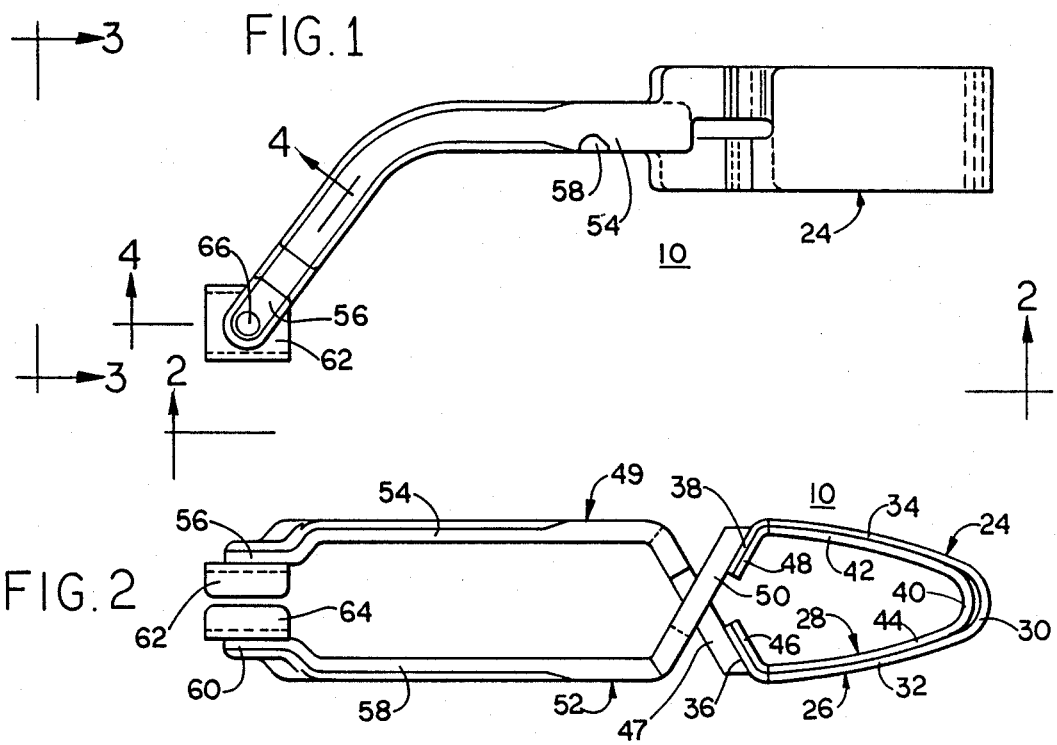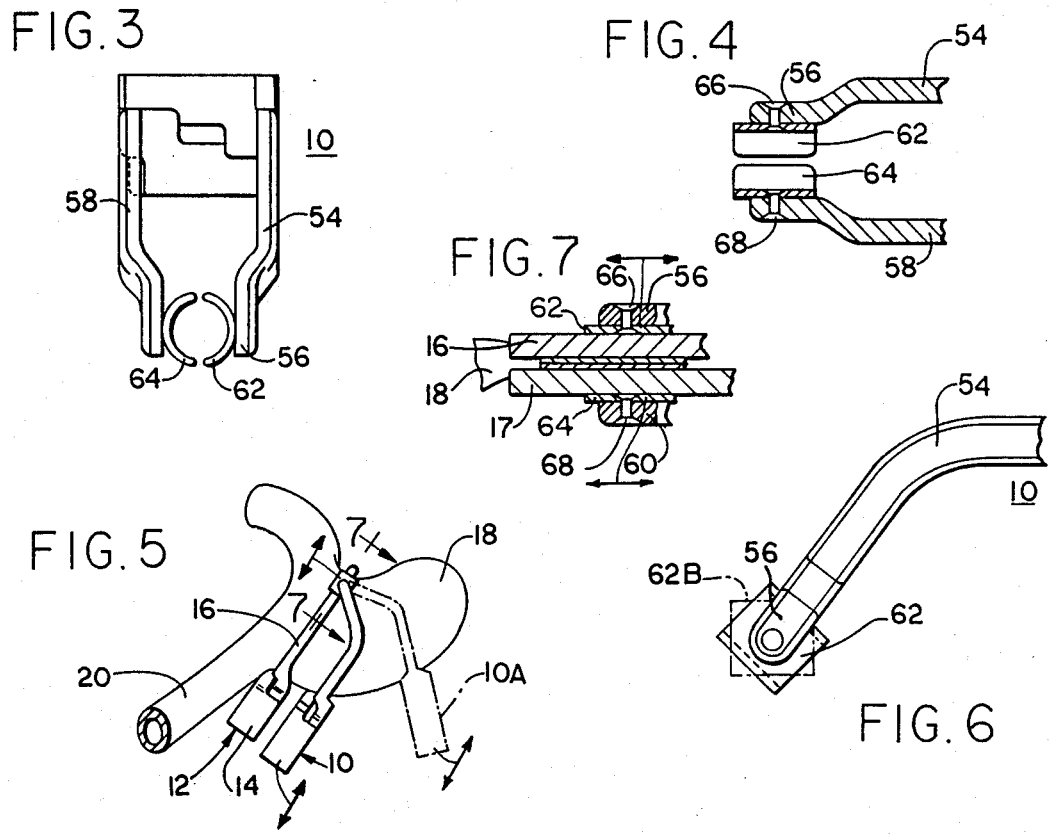

REINFORCING CLOSER FOR ANEURYSM CLIP

This invention relates to surgical clips for closing aneurysms and the like. More particularly, this invention relates to a device for holding jaws of a aneurysm clip in closed position.

An aneurysm clip can have long jaws which are urged toward closed position by a spring at ends of the jaws. In such an aneurysm clip, there can be portions of the jaws which are urged together with insufficient force to properly close the aneurysm while other portions of the jaws are urged together with greater force.

An object of this invention is to provide a closer device which can be mounted on the jaws of an aneurysm clip to urge portions of the jaws together where there is insufficient force provided by a spring of the aneurysm clip.

A further object of this invention is to provide such a closer device which can have auxiliary jaws which are urged together and which can be moved lengthwise of the jaws of the aneurysm clip to a selected position on the jaws of the aneurysm clip to supplement the force of the spring of the aneurysm clip.

A further object of this invention is to provide such a closer device in which a main portion of the closer device can bridge the aneurysm and can be swung about axes at the jaws of the closer device so that the main portion can be positioned at a convenient location.

A further object of this invention is to provide an aneurysm closing assembly including an aneurysm clip having elongated jaws and a closer for the jaws which can be located where desired along the jaws and urges the jaws to closed position.

A further object of this invention is to provide a closer device having a double layer spring for providing closing pressure.

Briefly, this invention provides an auxiliary closer device for use with an aneurysm clip having elongated jaws which are urged together by a spring at ends of the elongated jaws. The auxiliary closer device includes auxiliary jaws which can engage the jaws of the aneurysm clip and spring means for urging the auxiliary jaws toward each other. The auxiliary jaws can be pivotally attached to arm portions of the auxiliary device, and spring means can urge the arm portions in a direction to urge the auxiliary jaws toward each other to urge the portions of the jaws of the aneurysm clip engaged by the auxiliary jaws toward each other. The spring means can include two spring strips formed to a generally U-shape with end sections of the strips welded together and to jaw support members of the auxiliary closer device and central portions spaced so that the spring strips reinforce each other in providing spring pressure on jaws of the auxiliary closer device.

The above and other objects and features of the invention will be apparent to those skilled in the art to which this invention pertains from the following detailed description and the drawings, in which:

FIG. 1 is a plan view of a closer for an aneurysm clip constructed in accordance with an embodiment of this invention;

FIG. 2 is a view in side elevation of the closer for an aneurysm clip looking in the direction of the arrows 2—2 in FIG. 1;

FIG. 3 is a view in end elevation of the closer looking in the direction of the arrows 3—3 in FIG. 1;

FIG. 4 is a view in section taken generally on the line 4—4 in FIG. 1;

FIG. 5 is a perspective view of a fragmentary portion of a blood vessel having an aneurysm thereon and showing an aneurysm clip mounted on the aneurysm, the closer for the aneurysm clip being mounted on the aneurysm clip, an alternate position of a main portion of the closer being shown in dot-dash lines;

FIG. 6 is an enlarged fragmentary view of arms and jaws of the closer, an alternate position of the jaws of the closer being shown in dot-dash lines; and FIG. 7 is an enlarged fragmentary view in section taken on the line 7—7 in FIG. 5.

In the following detailed description and the drawing, like reference characters indicate like parts.

In the drawing is shown an aneurysm clip closer 10, which is constructed in accordance with an embodiment of this invention. The closer 10 can be mounted on an aneurysm clip 12 as shown in FIG. 5. The aneurysm clip 12 can be of usual construction and includes a central spring section 14 and elongated arms or jaws 16 and 17. The jaws 16 and 17 are urged together on a neck of an aneurysm 18 by action of the spring section 14. The aneurysm 18 is shown on a blood vessel 20, only a fragmentary portion of which is shown.

The clip closer 10 includes a central spring assembly 24 including an outer spring strip portion 26 and an inner spring strip portion 28. The outer spring portion 26 is generally U-shaped and includes an arcuate central section 30, arms 32 and 34 at opposite ends of the central section 30 and end flanges 36 and 38. The end flanges 36 and 38 are integrally formed with the arms 32 and 34, respectively, at ends of the arms 32 and 34 remote from the central section 30. The inner spring portion 28 similarly includes an arcuate central section 40, arms 42 and 44 at opposite ends of the central section 40, and flanges 46 and 48 integral with the arms 42 and 44, respectively, at ends of the arms 42 and 44 remote from the central section 40. The flanges 36 and 46 are welded together and to an arm portion 47 of a first main or closer jaw support member 49. The flanges 38 and 48 are welded together and to an arm portion 50 of a second main or closer jaw support member 52. The central sections 30 and 40 are spaced so that the spring portions 24 and 26 can both flex to put spring pressure on the jaw support members 49 and 52.

The jaw support member 49 includes an elongated body 54, which supports a head 56 spaced from the spring assembly 24. The body 54 can be angle-shaped, as shown in FIG. 1. The jaw support member 52 similarly includes an elongated body 58, which supports a head 60 spaced from the spring assembly 24. Jaw members 62 and 64 are pivotally mounted on the heads 56 and 60 by means of rivet members 66 and 68, respectively. The jaw members 62 and 64 are opposed to each other and can engage the jaws 16 and 17 of the aneurysm clip 12 to urge the jaws 16 and 17 to closed position. The jaw members 62 and 64 are arcuate in section and can be moved along the jaws 16 and 17 to a selected position where pressure is needed. In addition, the main portion of the closer 10 can be so positioned with respect to the jaw members 62 and 64 that the main portion is in a most convenient position, one position of the main portion being shown in full lines at 10 in FIG. 5 and an alternate position being shown at 10A in dot-dash lines. The bodies 54 and 58 of the jaw support members 49 and 52, respectively, are spaced to provide a space in which the aneurysm 18 can be received.

When the aneurysm closer 10 is to be mounted on the aneurysm clip 12, the jaws 62 and 64 can be swung as to a selected position such as the position shown in dot-dash lines at 62B in FIG. 6, and the jaw members can be opened and positioned on the jaws 16 and 18 at the appropriate position along the jaws 16 and 18 so that the closer does not unnecessarily interfere with surrounding tissues and the closer can provide closing pressure on the jaws 16 and 18 where required.

The clip closer can be formed from a metal alloy which is resistant to corrosion or deterioration in the presence of body fluids, such as stainless steel, and the spring portion 24 can be of such an alloy which is capable of forming a strong spring.

The aneurysm clip closer illustrated in the drawings and described above is subject to structural modification without departing from the spirit and scope of the appended claims.

Having described my invention, what I claim as new and desire to secure by letters patent is:

1. A device for closing jaws of an aneurysm clip which comprises a central spring portion, body members mounted on the central spring portion to be urged toward a closed position by the central spring portion, heads carried by the body members spaced from the central spring portion, and jaw members pivotally mounted on the heads and engageable with the jaws of the aneurysm clip to urge the jaws to closed position, the body members being spaced to receive the aneurysm therebetween, the spring portion including a pair of spring strip members, each of the spring strip members including an arcuate central section, arms extending from ends of the central section, and flanges at ends of the arms, each flange being rigidly attached to one of the flanges of the other spring strip member and to one of the body members, the arcuate sections being spaced so that the spring strip members supplement each other.

2. The combination of an aneurysm clip having elongated jaws with a device for closing the jaws of the aneurysm clip which comprises a central spring portion, body members mounted on the central spring portion to be urged toward a closed position by the central spring portion, heads carried by the body members spaced from the central spring portion, and jaw members mounted on the heads and engageable with the jaws of the aneurysm clip to urge the jaws to closed position, the body members being spaced to receive the aneurysm therebetween.

3. A device as in claim 2 in which the jaw members are pivotally mounted on the heads and are advanceable lengthwise of the jaws to selected position.

* * * * *